United States Patent
Shabani et al.

(10) Patent No.: US 11,246,899 B2
(45) Date of Patent: Feb. 15, 2022

(54) URTICA DIOICA EXTRACTS AND METHODS OF ISOLATING URTICA DIOICA EXTRACTS

(71) Applicant: SynHiTech Inc., Thornhill (CA)

(72) Inventors: Masoud Shabani, North York (CA); Mohammad Massumi, North York (CA)

(73) Assignee: SynHiTech Inc., Thornhill (CA)

( * ) Notice: Subject to any disclaimer, the term of this patent is extended or adjusted under 35 U.S.C. 154(b) by 139 days.

(21) Appl. No.: 16/437,865

(22) Filed: Jun. 11, 2019

(65) Prior Publication Data

US 2020/0000864 A1     Jan. 2, 2020

Related U.S. Application Data

(60) Provisional application No. 62/683,105, filed on Jun. 11, 2018.

(51) Int. Cl.
*A61K 36/185* (2006.01)
*A61P 3/08* (2006.01)
*A61K 9/19* (2006.01)

(52) U.S. Cl.
CPC ............. *A61K 36/185* (2013.01); *A61K 9/19* (2013.01); *A61P 3/08* (2018.01)

(58) Field of Classification Search
None
See application file for complete search history.

(56) References Cited

FOREIGN PATENT DOCUMENTS

| JP | 2014122183 A | * | 12/2014 | |
| RU | 2376024 C1 | * | 12/2009 | |
| WO | WO-2007087825 A1 | * | 8/2007 | ........... A61K 36/185 |

OTHER PUBLICATIONS

Belščak-Cvitanović (Nettle (*Urtica dioica* L.) extracts as functional ingredients for production of chocolates with improved bioactive composition and sensory properties., J Food Sci Technol, Dec. 2015, 52(12):7723-7734) (Year: 2015).*
Handmade Apothecary (http://www.handmadeapothecary.co.uk/blog/2017/9/1/know-your-nettles) Sep. 1, 2017 (Year: 2017).*
Ganzera (Urtica dioica Agglutinin (UDA)—Separation and Quantification of Individual Isolectins by Reversed Phase High Performance Liquid Chromatography, Chromatographia 2003, 58, Aug. (No. 3/4)) (Year: 2003).*
RU-2376024-C1 translated document (Year: 2009).*
JP2014122183A translated document (Year: 2014).*
Blumenthal M. New World plants; New World drugs. Allergy Proc 1992; 13(6):345-352.
Dasgupta A, Bernard DW. Herbal remedies: effects on clinical laboratory tests. Arch Pathol Lab Med 2006; 130(4):521-528.
Schulze-Tanzil G, de Souza P, Behnke B et al. Effects of the antirheumatic remedy Hox alpha—a new stinging nettle leaf extract—on matrix metalloproteinases in human chondrocytes in vitro. Histol Histopathol 2002; 17(2):477-485.
Bielory L. Complementary and alternative interventions in asthma, allergy, and immunology. Ann Allergy Asthma Immunol 2004; 93(2):S45-S54.
Ozen T, Korkmaz H. Modulatory effect of *Urtica dioica* L. (Urticaceae) leaf extract on biotransformation enzyme systems, antioxidant enzymes, lactate dehydrogenase and lipid peroxidation in mice. Phytomedicine 2003; 10(5):405-415.
Cetinus E, Kilinc M, Inane F, Kurutas EB, Buzkan N. The role of urtica dioica (urticaceae) in the prevention of oxidative stress caused by tourniquet application in rats. Tohoku J Exp Med 2005; 205(3):215-221.
Pierre S, Crosbie L, Duttaroy AK. Inhibitory effect of aqueous extracts of some herbs on human platelet aggregation in vitro. Platelets 2005; 16(8):469-473.
Bnouham M, Merhfour FZ, Ziyyat A et al. Antihyperglycemic activity of the aqueous extract of Urtica dioica. Fitoterapia 2003; 74(7-8):677-681.
Farzami B, Ahmadvand D, Vardasbi S, Majin FJ, Khaghani S. Induction of insulin secretion by a component of Urtica dioica leave extract in perifused Islets of Langerhans and its in vivo effects in normal and streptozotocin diabetic rats. J Ethnopharmacol 2003; 89(1):47-53.
Kavalali G, Tuncel H, Goksel S, Hatemi HH. Hypoglycemic activity of Urtica pilulifera in streptozotocin-diabetic rats. J Ethnopharmacol 2003; 84(2-3):241-245.
Ganzera M, Piereder D, Sturm S, Erdelmeier C, Stuppner H. Urtica dioica agglutinin: Separation identification, and quantitation of individual isolectins by capillary electrophoresis and capillary electrophoresis-mass spectrometry. Electrophoresis 2005; 26(9):1724-1731.
Liu TP, Liu IM, Cheng JT. Improvement of insulin resistance by panax ginseng in fructose-rich chow-fed rats. Horm Metab Res 2005; 37(3):146-151.
Liu TP, Lee CS, Liou SS, Liu IM, Cheng JT. Improvement of insulin resistance by acanthopanax senticosus root in fructose-rich chow-fed rats. Clin Exp Pharmacol Physiol 2005; 32(8):649-654.
Maroo J, Vasu VT, Aalinkeel R, Gupta S. Glucose lowering effect of aqueous extract of Enicostemma littorale Blume in diabetes: a possible mechanism of action. J Ethnopharmacol 2002; 81(3):317-320.

(Continued)

*Primary Examiner* — Susan Hoffman
*Assistant Examiner* — Jacob A Boeckelman
(74) *Attorney, Agent, or Firm* — Bereskin & Parr LLP (57) ABSTRACT

A method of isolating an extract of *Urtica dioica* is described herein. The method includes drying a raw material comprising *Urtica dioica*; grinding the raw material to form a ground raw material having a particle size in a range of about 0.5 to 1 mm; mixing the ground raw material with water to form a mixed raw material solution; and heating the mixed raw material solution to a temperature of about 100° C. and maintaining the temperature of about 100° C. for a period of time to form an extracted liquid solution.

7 Claims, 11 Drawing Sheets

(56) References Cited

OTHER PUBLICATIONS

Maroo J, Vasu VT, Gupta S. Dose dependent hypoglycemic effect of aqueous extract of Enicostemma littorale blume in alloxan induced diabetic rats. Phytomedicine 2003; 10(2-3):196-199.

Norberg A, Hoa NK, Liepinsh E et al. A novel insulin-releasing substance, phanoside, from the plant Gynostemma pentaphyllum. J Biol Chem 2004; 279(40):41361-41367.

Xie JT, Zhou YP, Dey L et al. Ginseng berry reduces blood glucose and body weight in db/db mice. Phytomedicine 2002; 9(3):254-258.

McCarty MF. Does bitter melon contain an activator of AMP-activated kinase? Med Hypotheses 2004; 63(2):340-343.

Rathi SS, Grover JK, Vats V. The effect of Momordica charantia and Mucuna pruriens in experimental diabetes and their effect on key metabolic enzymes involved in carbohydrate metabolism Phytother Res 2002; 16(3):236-243.

Barham D, Trinder P. An improved colour reagent for the determination of blood glucose by the oxidase system. Analyst 1972; 97(151):142-145.

McEvoy RC, Thomas NM, Hellerstrom C, Ginsberg-Fellner F, Moran TM. Multiple low-dose streptozotocin-induced diabetes in the mouse: further evidence for involvement of an anti-B cell cytotoxic cellular auto-immune response. Diabetologia 1987; 30(4):232-238.

* cited by examiner

URTICA DIOICA EXTRACTS AND METHODS OF ISOLATING URTICA DIOICA EXTRACTS

CROSS-REFERENCE

This application claims the benefit of U.S. Provisional Patent Application No. 62/683,105, filed Jun. 11, 2018, and the entire contents of U.S. Provisional Patent Application No. 62/683,105 is hereby incorporated by reference.

TECHNICAL FIELD

The embodiments disclosed herein relate to therapeutic natural products, and, in particular to *Urtica dioica* extracts, antidiabetic activity of *Urtica dioica* extracts, anti-hyperglycemic effects of peptides discovered in extracts of *Urtica dioica* and methods of isolating *Urtica dioica* extracts.

BACKGROUND

Approximately 400 million people worldwide suffer from diabetes. Approximately 5 to 10% of all diabetic patients are suffering from type 1 diabetes (T1D), in which they lose the pancreatic β-cells by the autoimmune reaction. In type 2 diabetes (T2D), muscle and fat cells of the patient become resistant to insulin uptake.

Stinging nettle is a plant that is native to Eurasia and can now be found throughout the world. Stinging nettle is a staple among Western herbal practitioners. Its genus name *Urtica* is derived from euro, to burn, or urere, meaning to sting. Stinging nettle leaf, often mixed with stem and sometimes seed, is sold in fresh, dried, and freeze-dried form. The fresh leaves are bright vibrant green, with strongly serrated edges, and a clearly visible venation on the lower leaf surface. Both the leaves, and stems are covered with erect and bristly glandular hairs that contain, among other compounds, acetylcholine, formic acid, 5-hydroxytryptamine, and histamine. Fresh material will typically cause skin irritation if handled without gloves. Stinging nettle leaves are commonly used to treat a variety of conditions including rheumatic conditions, seasonal allergies, and the presence of kidney stones. Stinging nettle also is known to have a diuretic effect, hemostatic activity, and blood glucose lowering properties.

Despite the fact that diabetes and its complications have long been treated with a wide range of herbal preparations, little is known about the identity and mechanism of action of the active components of these herbal treatments. In addition, there is very little comparable knowledge of how medicinal therapies act to treat diabetes. Determining the cellular mechanism of action of the active herbal components is an important step towards characterizing their general physiological function. The glucose-lowering effect of most herbal derivatives is attributed to alterations in insulin secretion. It is still unclear whether there are herbal extracts which mimic the function of insulin by directly activating the insulin receptor. For instance, bitter melon extract has been reported to increase expression of GLUT4 in the plasma membrane of skeletal muscle through activation of AMP-activated kinase and cinnamon extract has been shown to stimulate the insulin receptor of skeletal muscle and to enhance IRS-1 tyrosine phosphorylation levels in rodents.

Accordingly, there is a need for new or improved characterizations of *Urtica dioica* extracts and methods of isolating *Urtica dioica* extracts.

SUMMARY

According to some embodiments, a method of isolating an extract of *Urtica dioica* is provided. The method includes drying a raw material comprising *Urtica dioica*; grinding the raw material to form a ground raw material having a particle size in a range of about 0.5 to 1 mm; mixing the ground raw material with water to form a mixed raw material solution; and heating the mixed raw material solution to a temperature of about 100° C. and maintaining the temperature of about 100° C. for a period of time to form an extracted liquid solution including the extract of *Urtica dioica*.

According to some embodiments, the method also includes lyophilizing the extracted liquid solution.

According to some embodiments, the drying occurs at a temperature in a range of about 20° C. to 30° C.

According to some embodiments, the drying occurs at a temperature of about 25° C.

According to some embodiments, the *Urtica dioica* is dried for a duration in a range of about 1 to 15 days.

According to some embodiments, the *Urtica dioica* is dried for a duration of about 7 days.

According to some embodiments, the ground raw material is mixed with water in a ratio in a range of about 1 kg to ground raw material to 3 kg of water to form the mixed raw material solution.

According to some embodiments, the mixed raw solution is heated until the extracted liquid solution has a concentration of an Urdi-1 extract that is not less than 250 mg/L.

According to some embodiments, the ground raw material and the water are mixed in a ratio of about 3 kg of water to 1 kg to ground raw material.

According to some embodiments, a method for treating diabetes in a mammal is provided. The method includes administering to said mammal an extract of *Urtica dioica*, said extract isolated using a method described herein.

According to some embodiments, the mammal is a human.

According to some embodiments, the human is a male.

According to some embodiments, the human is a female.

According to some embodiments, a method of modulating blood glucose level in a mammal is provided. The method includes administration of an effective dose of an extract of *Urtica dioica*.

According to some embodiments, the blood glucose level is decreased.

According to some embodiments, a pharmaceutical composition comprising an effective dose of an extract of *Urtica dioica* is provided herein.

According to some embodiments, the extract of *Urtica dioica* is an antidiabetic substance.

According to some embodiments, the extract of *Urtica dioica* can increase the uptake of blood glucose by facilitating the transferring of the glucose into muscle cells.

According to some embodiments, administration of the extract of *Urtica dioica* may not have obvious side effects.

According to some embodiments, the extract of *Urtica dioica* may increase uptake of glucose in both Type 1 and Type 2 diabetic patients.

According to some embodiments, the extract of *Urtica dioica* is a peptide composed of amino acids.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings.

The skilled person in the art will understand that the drawings, further described below, are for illustration purposes only. The drawings are not intended to limit the scope of the applicant's teachings in any way. Also, it will be appreciated that for simplicity and clarity of illustration, elements shown in the figures have not necessarily been drawn to scale. For example, the dimensions of some of the elements may be exaggerated relative to other elements for clarity. Further aspects and features of the example embodiments described herein will appear from the following description taken together with the accompanying drawings.

DETAILED DESCRIPTION

Various apparatuses, methods and compositions are described below to provide an example of at least one embodiment of the claimed subject matter. No embodiment described below limits any claimed subject matter and any claimed subject matter may cover apparatuses and methods that differ from those described below. The claimed subject matter are not limited to apparatuses, methods and compositions having all of the features of any one apparatus, method or composition described below or to features common to multiple or all of the apparatuses, methods or compositions described below. Subject matter that may be claimed may reside in any combination or sub-combination of the elements or process steps disclosed in any part of this document including its claims and figures. Accordingly, it will be appreciated by a person skilled in the art that an apparatus, system or method disclosed in accordance with the teachings herein may embody any one or more of the features contained herein and that the features may be used in any particular combination or sub-combination that is physically feasible and realizable for its intended purpose.

Furthermore, it is possible that an apparatus, method or composition described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

It will also be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the result is not significantly changed. These terms of degree should be construed as including a deviation of the modified term, such as 1%, 2%, 5%, or 10%, for example, if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

In spite of the technologies that have been developed, there remains a need in the field for improvements in the development methods and techniques for isolating extracts of *Urtica dioica*.

Generally, a method of isolating an extract of a natural substance purified from stinging nettle (*Urtica dioica*) is described herein. The method can be used to isolate the Urdi-1 extract of *Urtica dioica*, which may be used to lower blood glucose levels in patients with diabetes, particularly type II diabetes. For instance, an aqueous Urdi-1 extract may improve glucose uptake in insulin-sensitive tissues.

The present disclosure provides a method for producing fractionalized extracts of *Urtica dioica*. The fractionalized extracts of *Urtica dioica* may be separated by High-Performance Liquid Chromatography (HPLC). The Urdi-1 extract has been identified as a potentially anti-diabetic fraction in the extract. The Urdi-1 fraction may for example reverse hyperglycemia in diabetic mice.

Figure 1:
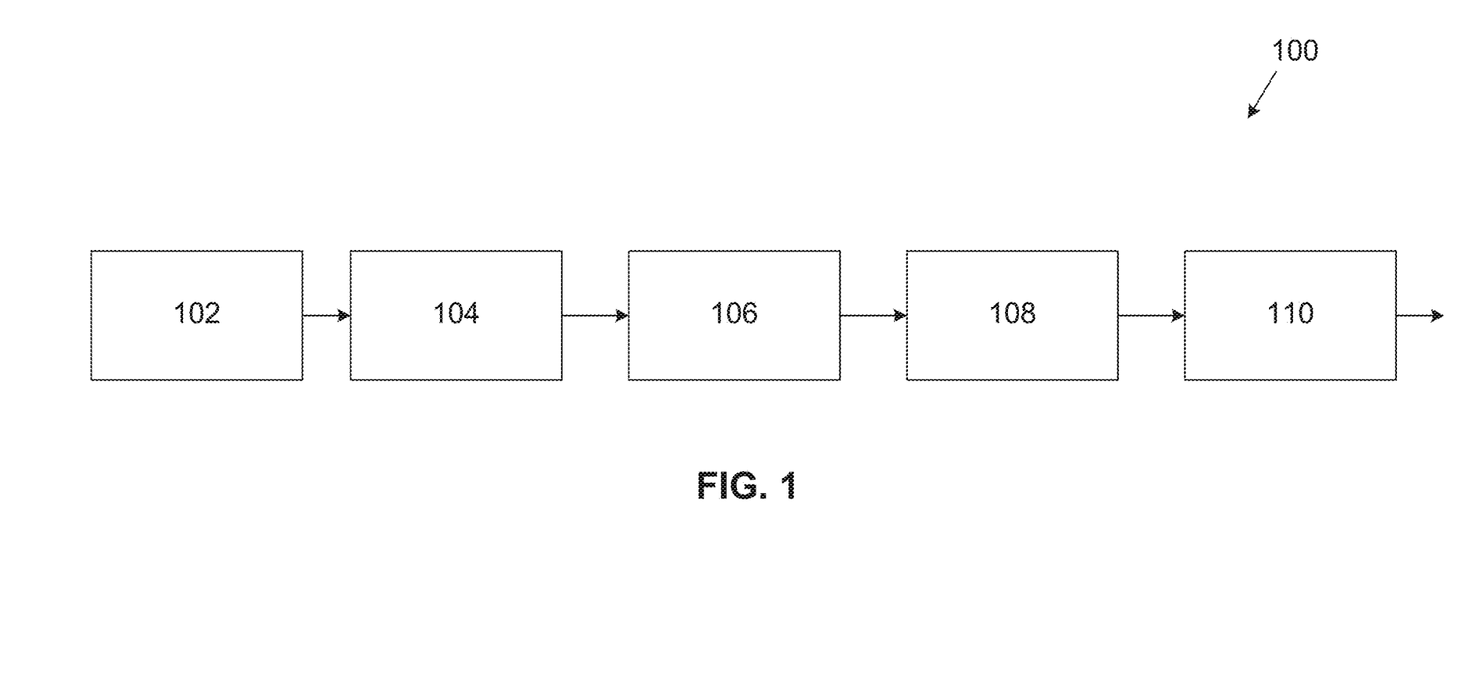
FIG. 1 is a schematic diagram showing a process for isolating the Urdi-1 extract of *Urtica dioica*, according to one embodiment.

Referring now to FIG. 1, illustrated therein is a method 100 of isolating the Urdi-1 fraction of *Urtica dioica*.

At drying step 102, a raw material containing *Urtica dioica* is to produce a dried raw material. The raw material can consist of, consist essentially of or comprise a raw form of *Urtica dioica*. For instance, the raw material can consist of, consist essentially of or comprise mixture of leaves and stems of *Urtica dioica*. In some embodiments, the raw material is a mixture of leaves and stems having a ratio in a range of about 1:10 leaves to stems to about 1:1 leaves to stems. In some embodiments, the raw material is a mixture of leaves and stems having a ratio about 1:3 leaves to stems.

In some embodiments, the raw material consisting of, consisting essentially of or comprising *Urtica dioica* is dried at a temperature in a range of about 20° C. to about 50° C., or in a range of about 20° C. to about 40° C. to form a dried raw material. In some embodiments, the raw material consisting of, consisting essentially of or comprising *Urtica dioica* is dried at a temperature of about 25° C. to form the dried raw material.

In some embodiments, the raw material consisting of, consisting essentially of or comprising *Urtica dioica* is dried for a duration in a range of about 1 day to about 7 days, or in a range of about 3 days to about 7 days to form the dried raw material. In some embodiments, the raw material consisting of, consisting essentially of or comprising *Urtica dioica* is dried for a duration of about 7 days to form the dried raw material.

At grinding step 104, the dried raw material is subjected to size reduction to form a ground raw material having an average particle size in a range of about 0.5 to about 1 mm. In some embodiments, the dried raw material is ground in a grinding machine to form the ground raw material having an average particle size in a range of about 0.5 to about 1 mm.

At mixing step 106, the ground raw material is mixed with water to form a mixed raw material solution. In some embodiments, the ground raw material is mixed with water in a ratio in a range of about 1 kg of ground raw material to about 3 kg of water. In some embodiments, the mixing of the ground raw material and the water occurs in a boiling tank that is connecting to a distillation system. In some embodiments, during the mixing, the water is at a temperature in a range of about 15° C. to about 30° C., or is about 20° C. (i.e. ambient temperature).

At heating step 108, the mixed raw material solution is heated to a desired temperature and maintained at the desired temperature for a period of time to produce a vapor that can be collected using the distillation system, and an extracted liquid solution. In some embodiments, the desired temperature of heating step 108 is in a range of about 100° C. to about 150° C. In other embodiments, the desired temperature is about 100° C. The extracted liquid solution can be collected in sterile vessel.

In some embodiments, the mixed raw material solution is heated to a temperature in a range of about 70° C. to about 100° C., or to about 100° C., and maintained at a temperature in a range of about 70° C. to about 100° C., or at about 100° C., so the mixed raw material solution boils. In some embodiments, maintaining the mixed raw material solution at a temperature in a range of about 70° C. to about 100° C., or at about 100° C., provides for the structure of the Urdi-1 extract to be preserved while other components of the mixed raw material solution such as but not limited to other Urdi fractions, alkaloids, fractions of pectins and the like are removed as vapor. During boiling, the mixed raw material solution produces the vapor and the extracted liquid solution. The mixed raw material solution is generally maintained at the desired temperature (i.e. boiled) until a concentration of the Urdi-1 extract in the extracted liquid solution is not less than about 100 mg/L, or not less than about 200 mg/L, or not less than about 250 mg/L. The concentration of the Urdi-1 extract in the extracted liquid solution can be detected by spectrophotometry at 225 nm of picked samples.

The concentration of the Urdi-1 extract in the extracted liquid solution is an important factor because, in some embodiments, if the concentration of the Urdi-1 extract in the extracted liquid solution is less than about 250 mg/L, the distillate may include other components such as but not limited to other Urdi fractions, alkaloids, fractions of pectins and the like.

At a lyophilizing step 110, the extracted liquid solution can be aliquoted into smaller volumes (such as but not limited to 100 mL volumes) in sterile plastic bags, for example, and concentrated by a lyophilizing system operating at about −45° C. and under 0.06 mbar atmospheric pressure for a duration of about 48 hrs. The lyophilized product can be evaluated by HPLC with respect to Urdi-1 concentration (mg/L) and used to formulate Urdi-1 based on the concentration indicated in Table 1.

The Urdi-1 fraction is also characterized herein. First, the active component of the extract has been determined by an analysis of the optical features of the three different *Urtica dioica* fractions (referred herein as Urdi-1, Urdi-2 and Urdi-3; see FIG. 2).

Figure 2:
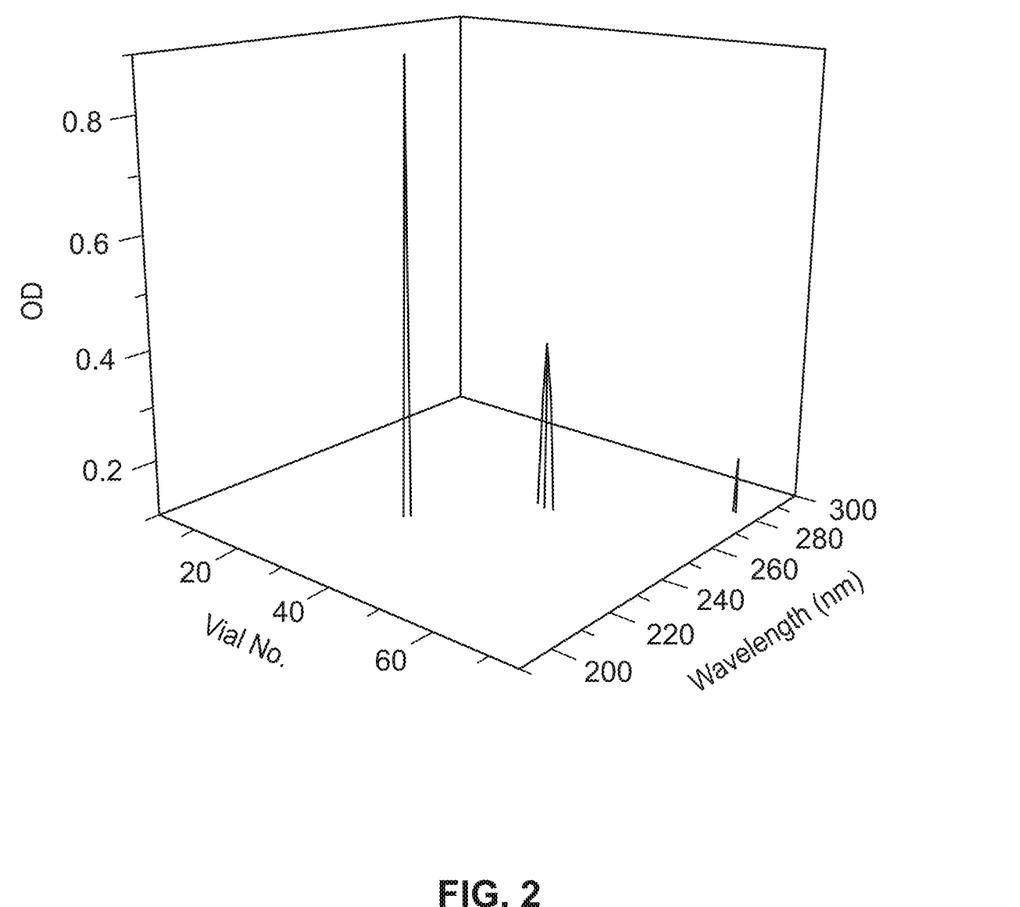
FIG. 2 is a graph showing maximum wavelengths of each of three fractions (Urdi-1, Urdi-2 and Urdi-3) separated from crude aqueous Urdi extract by Thin Layer Chromatography (TLC).

As shown in FIG. 2 (described below in the Examples section) three *Urtica dioica* fractions of can be separated from crude aqueous *Urtica dioica* extract by Thin Layer Chromatography. Ultraviolet absorbance spectrums from 190 to 300 nm can be used to obtain the corresponding maximum wavelengths of each fraction. For instance, the Urdi-1 fraction is identified as the fraction having a strong intensity at about 223 nm. Referring to FIG. 2, the elution volume for each fraction (Urdi-1, Urdi-2 and Urdi-3) is shown on the Y-axis. The flow rate and column conditions are described in the methods section, below.

The presence of a maximum absorbance at about 195 nm and about 223 nm can be attributed to the presence of a peptide bond. Having a comparatively low intensity at about 223 nm, the Urdi-1 peak was attributed to a forbidden symmetry transition of a peptide bond, while a strong transition of a peptide bond occurred at 195 nm. Under the conditions applied in Thin Layer Chromatography, the peptides eluted were those ranging in size from 500-2000 Da.

The presence of a peptidic structure was confirmed by an N-terminus determination assay. The results of the N-terminus determination assay suggested the presence of a lysine residue in the N-terminus position of the Urdi-1 fraction.

Figure 3:
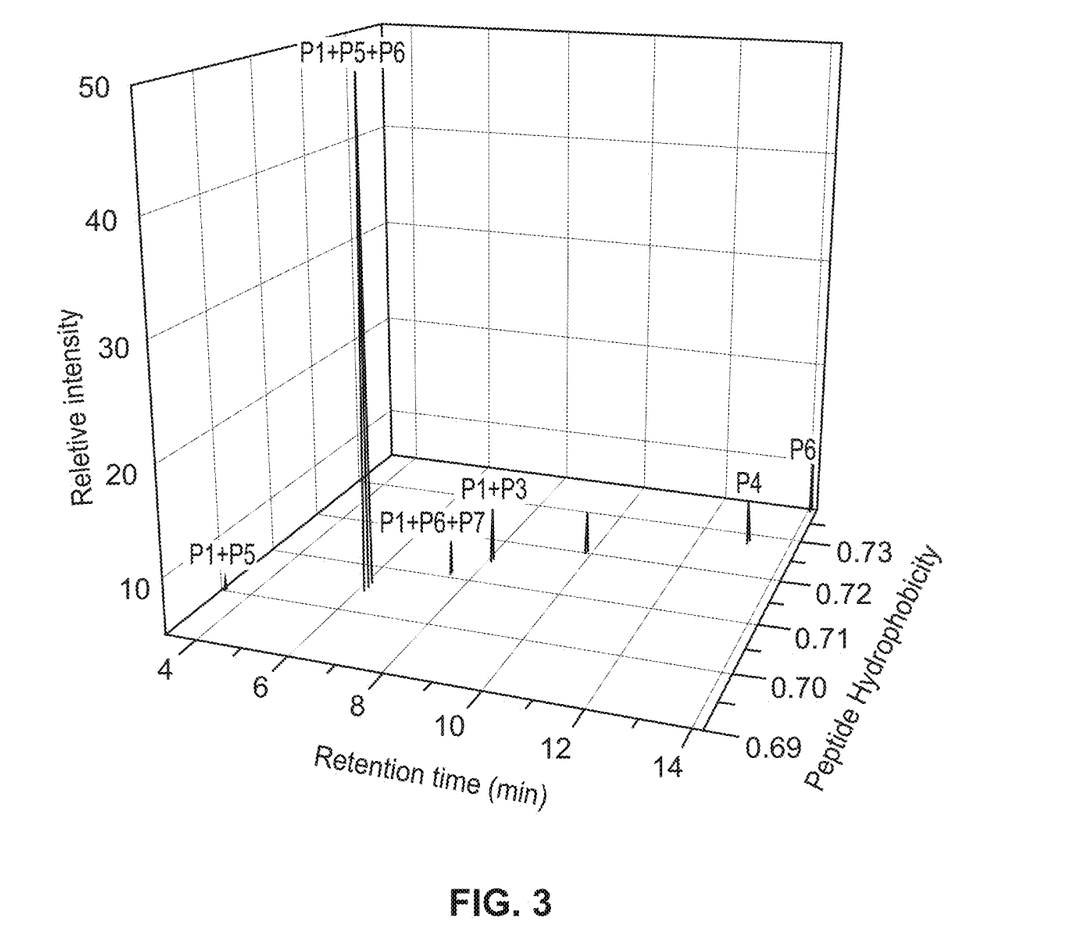
FIG. 3 is a graph showing advanced purification and identification of Urdi-1.

The Urdi-1 fraction produces one main fraction at 25% ACN (Rt=6.10 min) as well as 6 minor fractions. Further analysis of the main HPLC peak reveals that the Urdi-1 fraction is composed of a peptidic compound. The Z axis of FIG. 3 shows the polarity of the HPLC solvent system. It should be noted that the Urdi-1 fraction was diluted at 75% ddH$_2$O and thus appears to have a distinct hydrophilic feature.

Figure 4A:
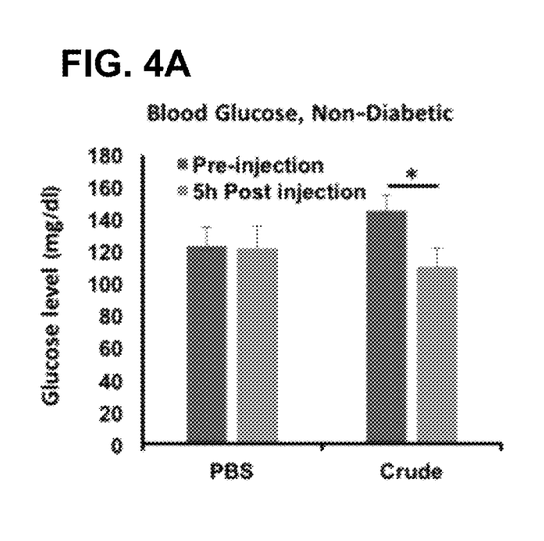
FIG. 4A is a graph showing the glucose lowering effect of Urdi-1.
Figure 4B:
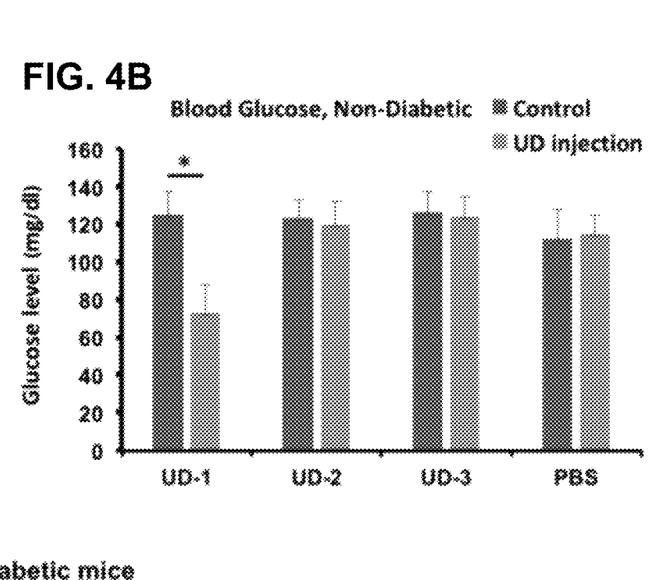
FIGS. 4B and 4C are graphs showing the glucose-lowering effect of Urdi-1 in normal and diabetic mice, respectively.
Figure 4C:
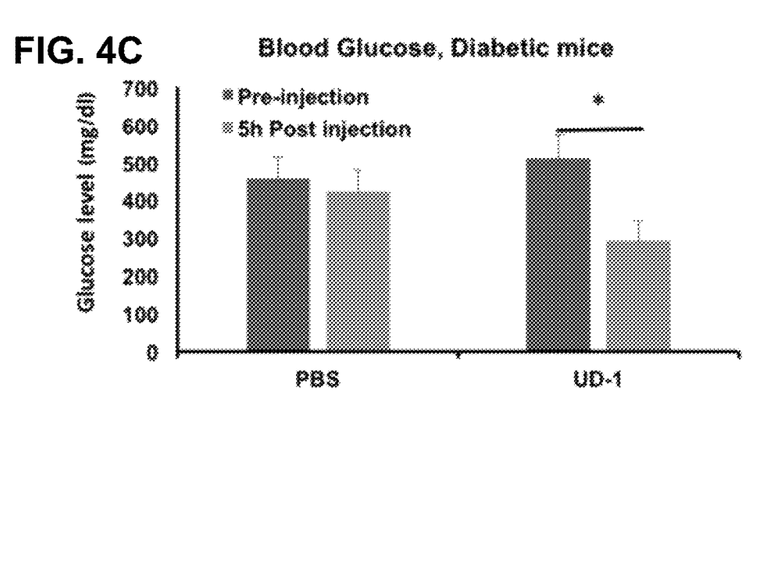
Figure 5A:
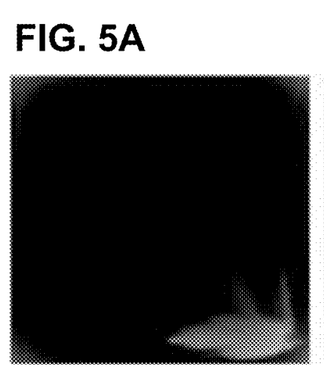
FIG. 5A shows the migration pattern of standard dansylated lysine.
Figure 5B:
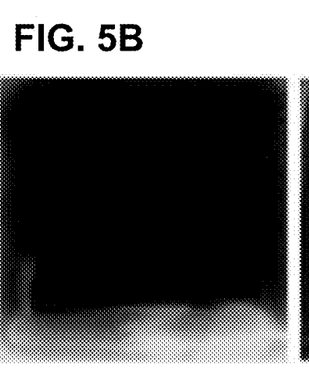
FIG. 5B shows the migration pattern of the N-terminus derived amino acids of Urdi-1 on thin layer chromatography.
Figure 5C:
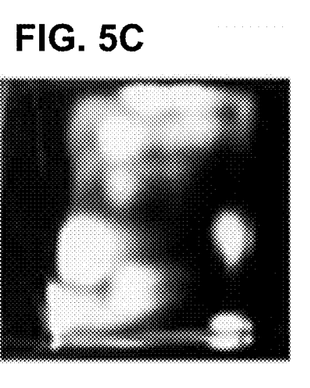
FIG. 5C and FIG. 5D show migration patterns of other amino acids.
Figure 5D:
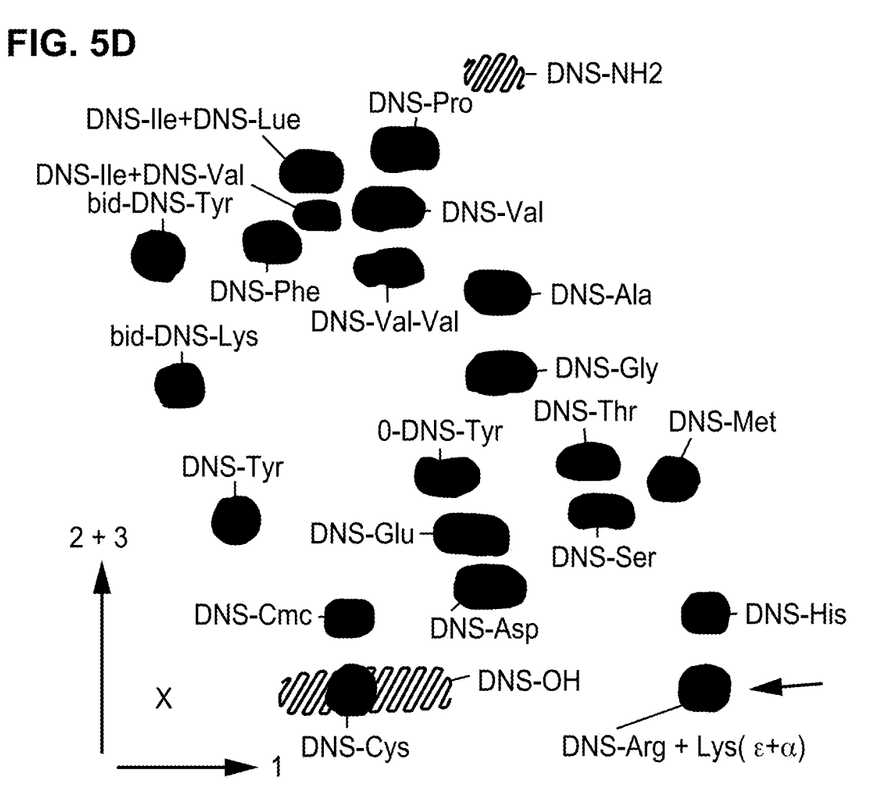

Referring now to FIGS. 4A to 4C, the three Urdi fractions (Urdi-1, Urdi-2 and Urdi-3) were tested for their glucose lowering effect. Of the three, Urdi-1 appears to have a significant glucose lowering effect (see FIG. 4A). FIGS. 4B and 4C illustrate the glucose-lowering effect of the Urdi-1 fraction in normal and diabetic mice, respectively. The maximum glucose lowering effect occurs approximately 5 hours after treatment.

Further clarification of the identity of the effective component of Urdi-1 was provided by amino acid analysis of the HPLC purified fraction of Urdi-1 (see FIG. 5). The dansyl chloride method was used to determine the amino acid occupying the N-terminus of the main component of Urdi-1. The migration pattern of standard dansylated lysine (FIG. 5A) can be compared with the N-terminus derived amino acids of Urdi-1 (FIG. 5B) on thin layer chromatography, confirming that a lysine residue occupied this position. FIGS. 4C and 4D show the migration patterns of further amino acids.

Figure 6A:
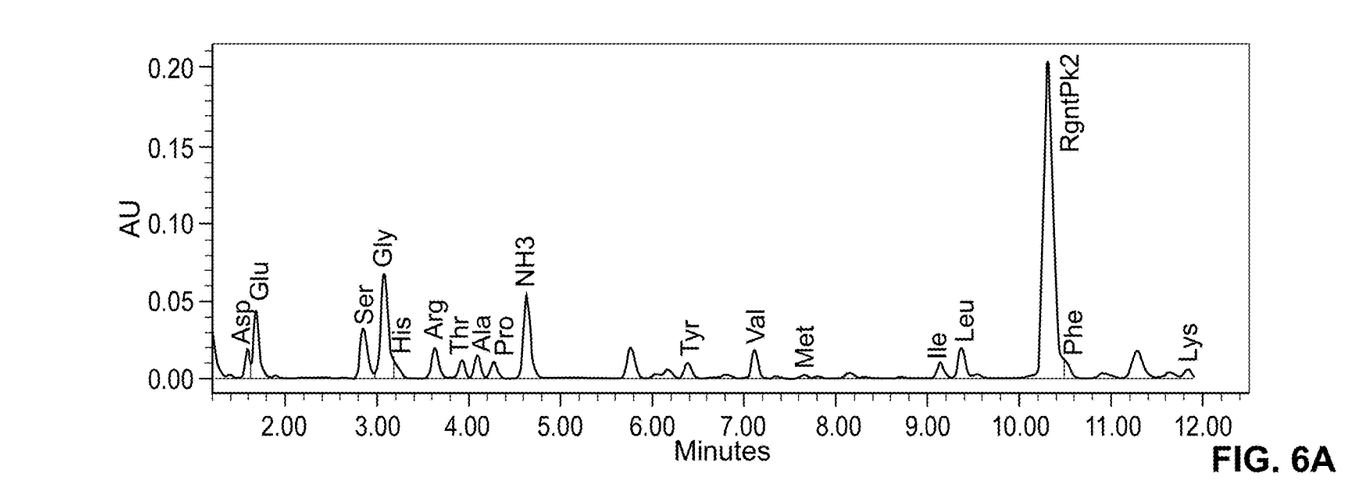
FIG. 6A shows the amino acid content of the main fraction of the Urdi-1 extract.
Figure 6B:
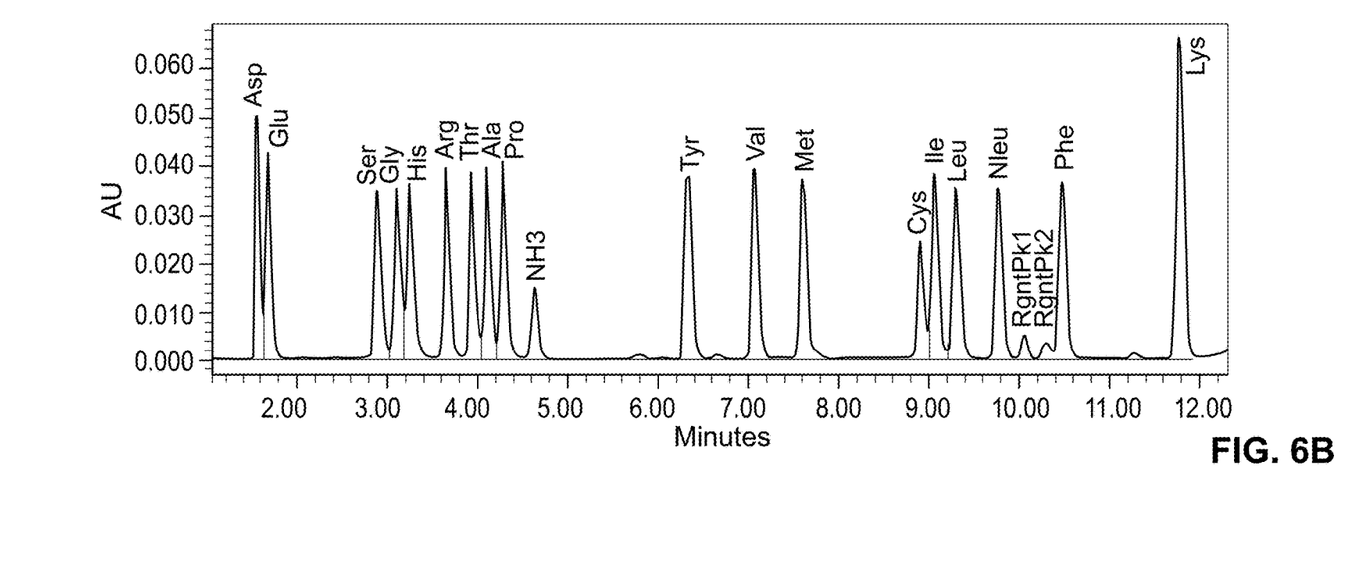
FIG. 6B shows a chromatography profile for standard amino acids.

Referring now to FIG. 6, FIG. 6A shows the amino acid content of the Urdi-1 fraction. FIG. 6B shows a chromatography profile for standard amino acids.

Figure 7A:
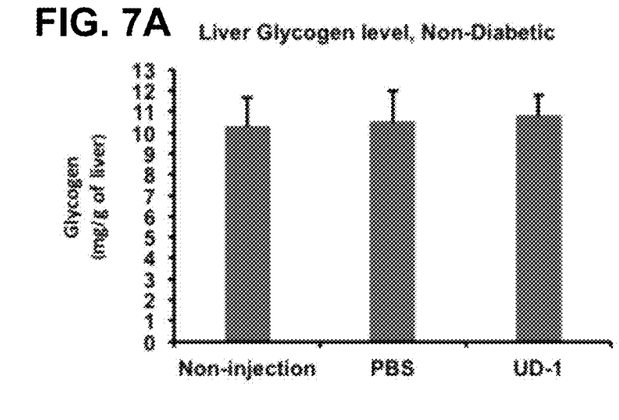
FIG. 7A is a graph showing the effects of Urdi-1 on liver glycogen in fasting mice.
Figure 7B:
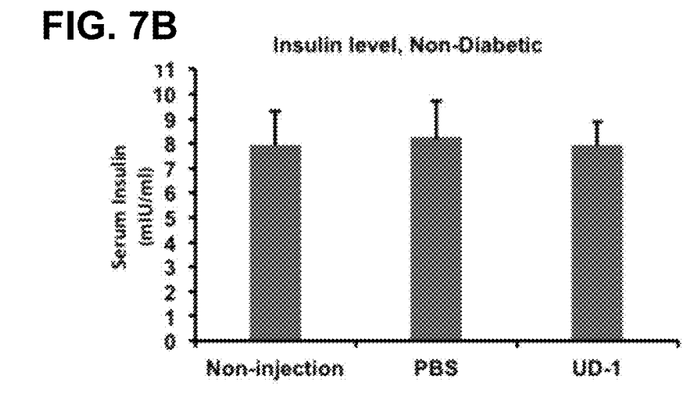
FIG. 7B is a graph showing the effects of Urdi-1 on serum insulin in fasting mice.
Figure 7C:
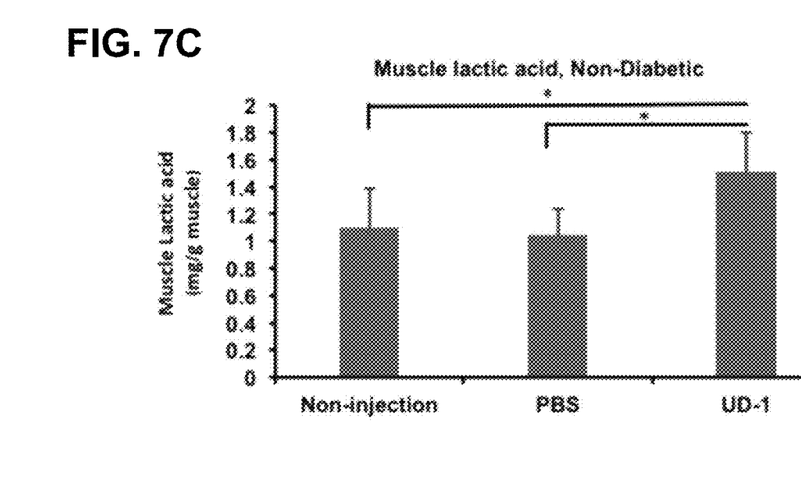
FIG. 7C is a graph showing the effects of Urdi-1 on muscle lactate in fasting mice.

Referring now to FIG. 7, the effects of Urdi-1 on different metabolic variables is shown therein. For instance, fasting mice were treated with Urdi-1 (25 mg/kg body weight) and after 5 hours were sacrificed. The muscles and livers of the mice were then subjected to a biochemical assay. While neither liver glycogen (FIG. 7A) nor serum insulin (FIG. 7B) show notable variation, muscle lactate levels (FIG. 7C) increases significantly upon intraperitoneal treatment of Urdi-1.

Figure 8A:
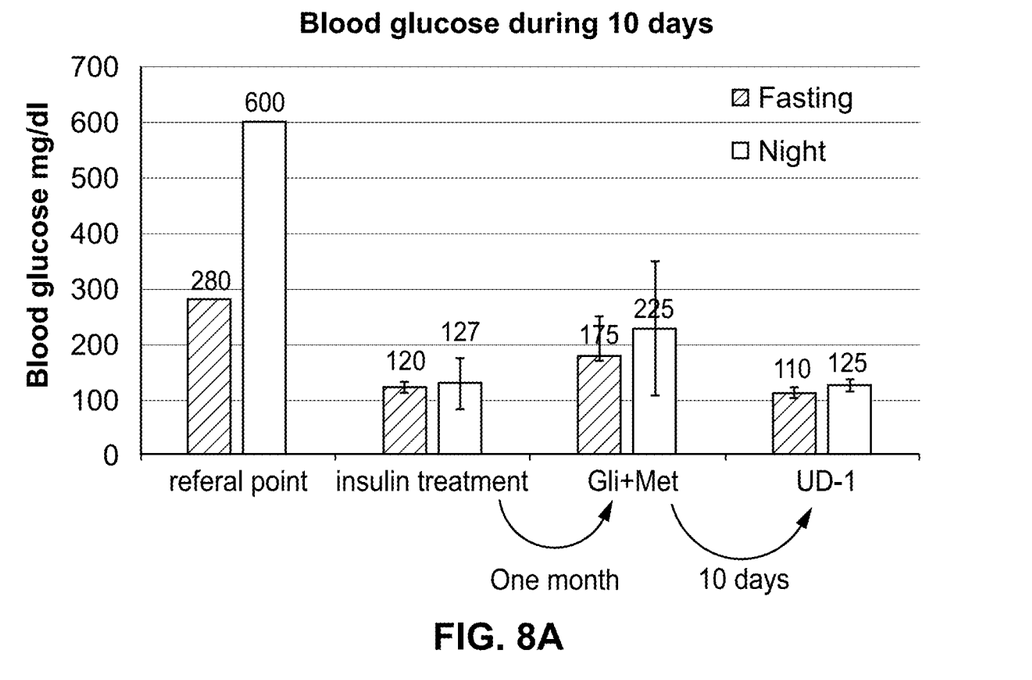
FIG. 8A is a graph showing blood glucose levels in Type 2 diabetic male patients treated by Urdi-1 for ten days.
Figure 8B:
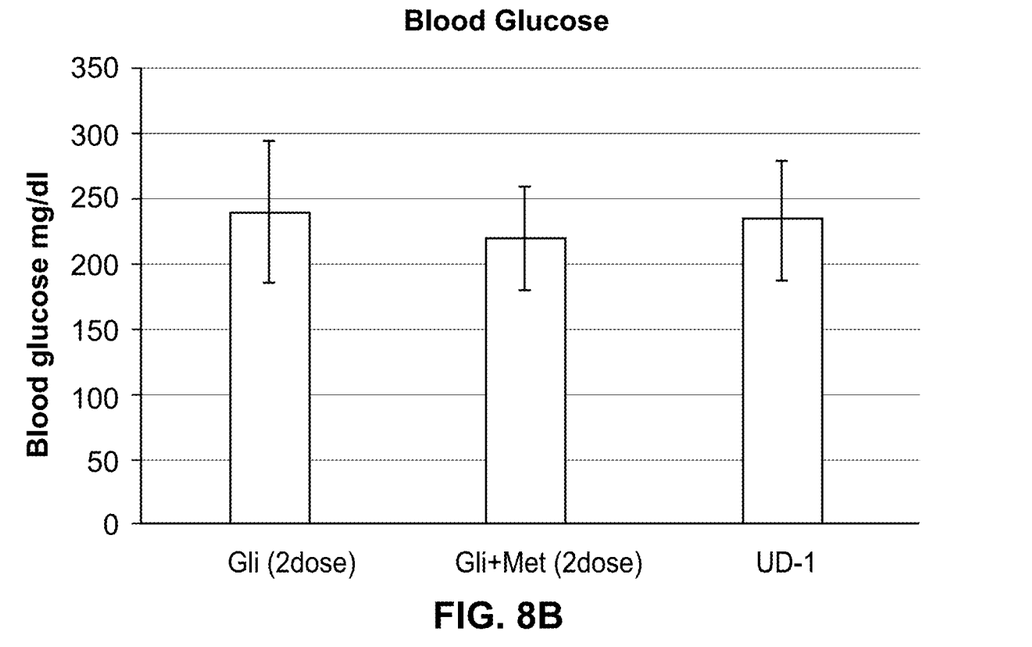
FIG. 8B is a graph showing night blood glucose levels in Type 2 diabetic female patients treated by Urdi-1 for two months.
Figure 8C:
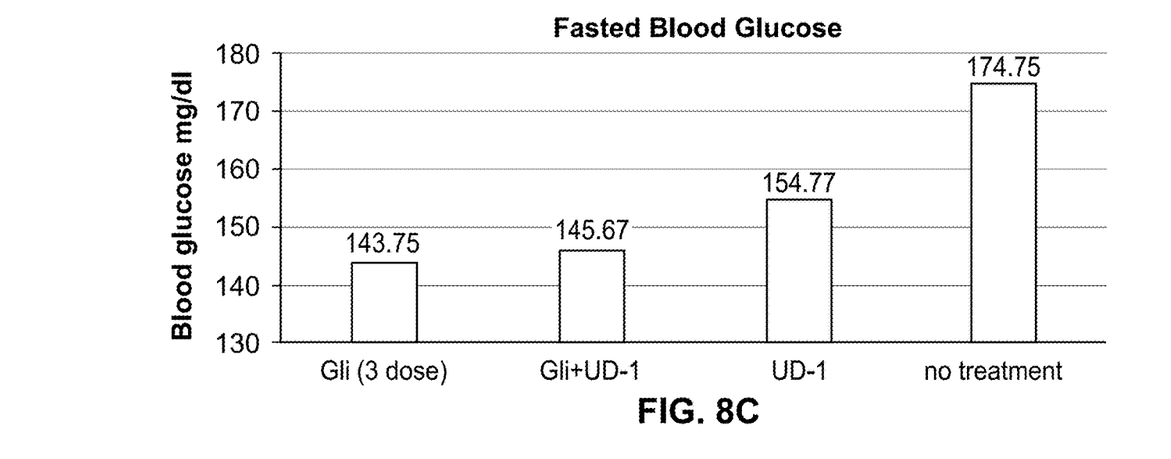
FIG. 8C is a graph showing fasted blood glucose levels in Type 2 diabetic male patients treated by Urdi-1 for three months.
Figure 8D:
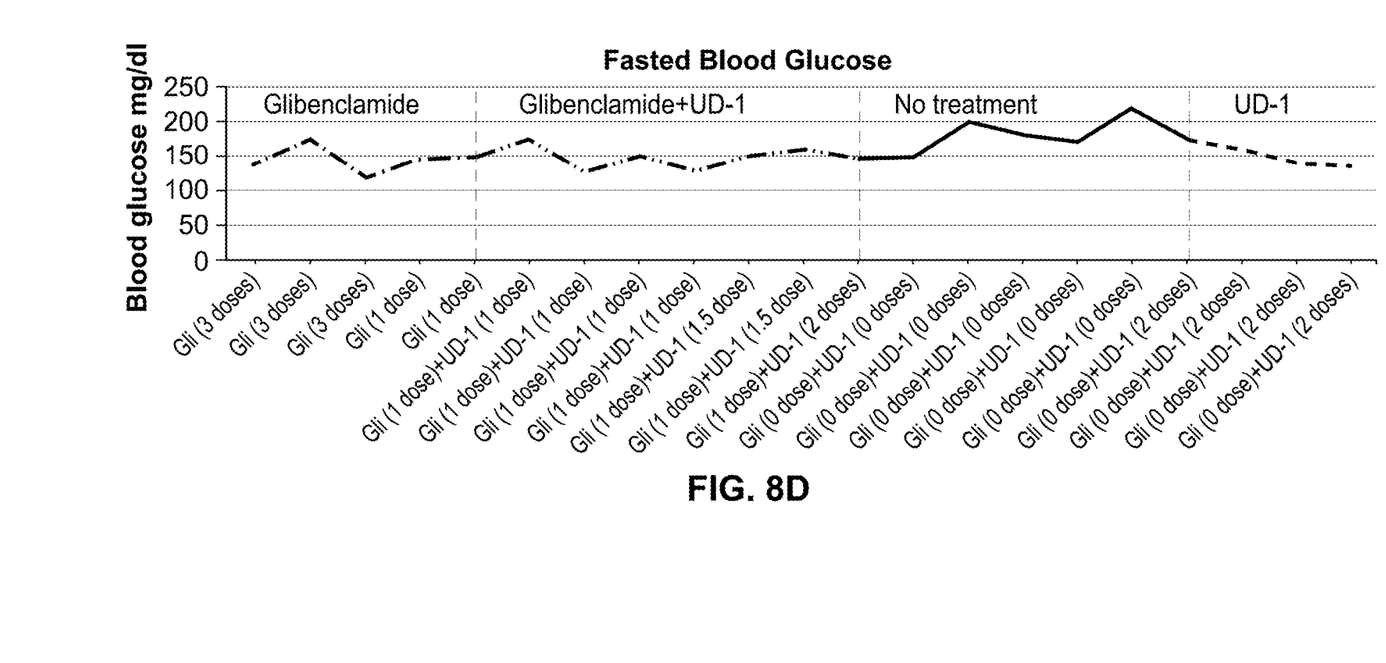
FIG. 8D shows a treatment regime for the fasted blood glucose levels shown in FIG. 8C.
Figure 8E:
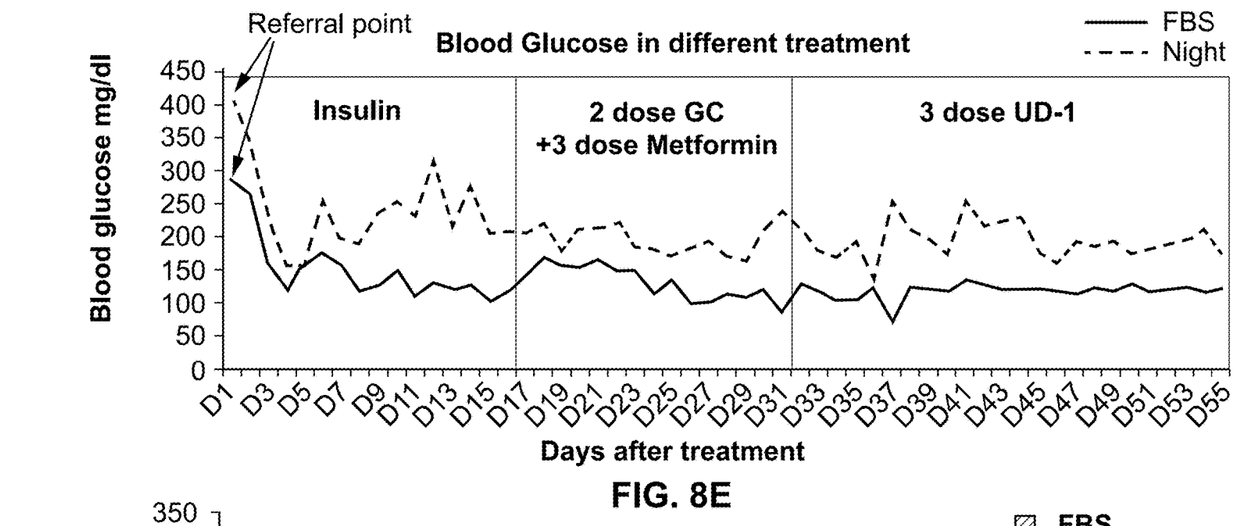
FIG. 8E is a graph showing fasting and night blood glucose levels in Type 2 diabetic male patients treated by Urdi-1 for three months.
Figure 8F:
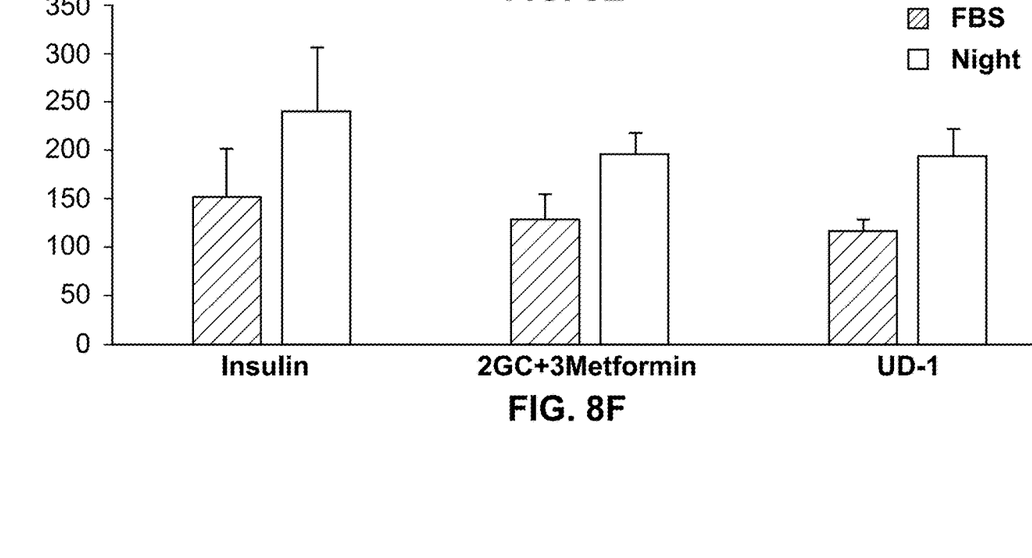
FIG. 8F is a graph showing average values of the patient data shown in FIG. 8E.
Figure 8G:
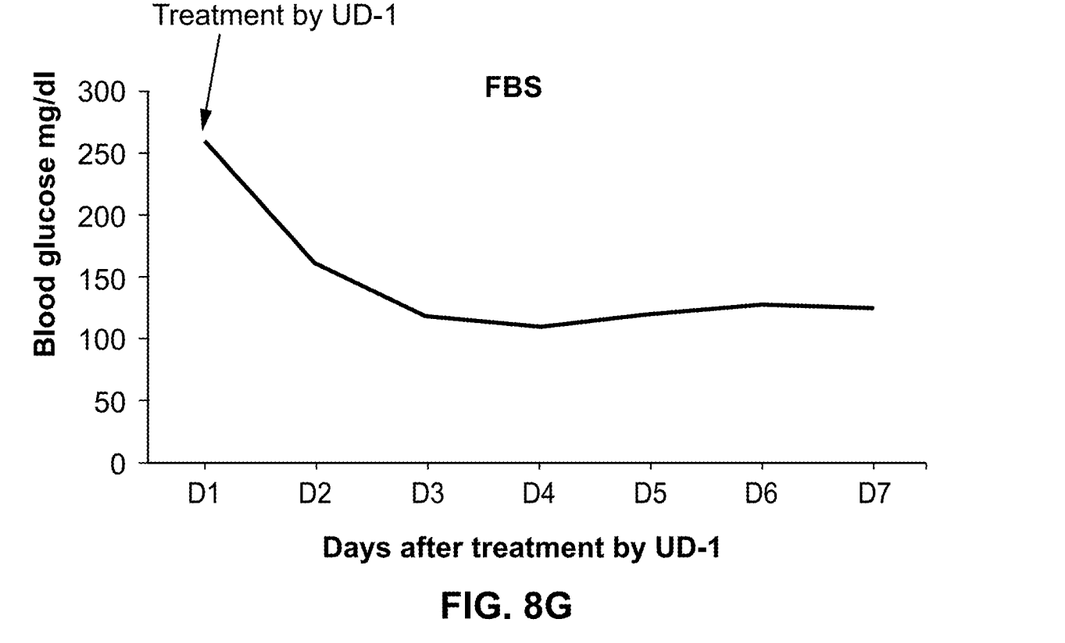
FIG. 8G is a graph illustrating fasting blood glucose levels in a female Type 2 diabetic patient treated by Urdi-1 for two months.
Figure 8H:
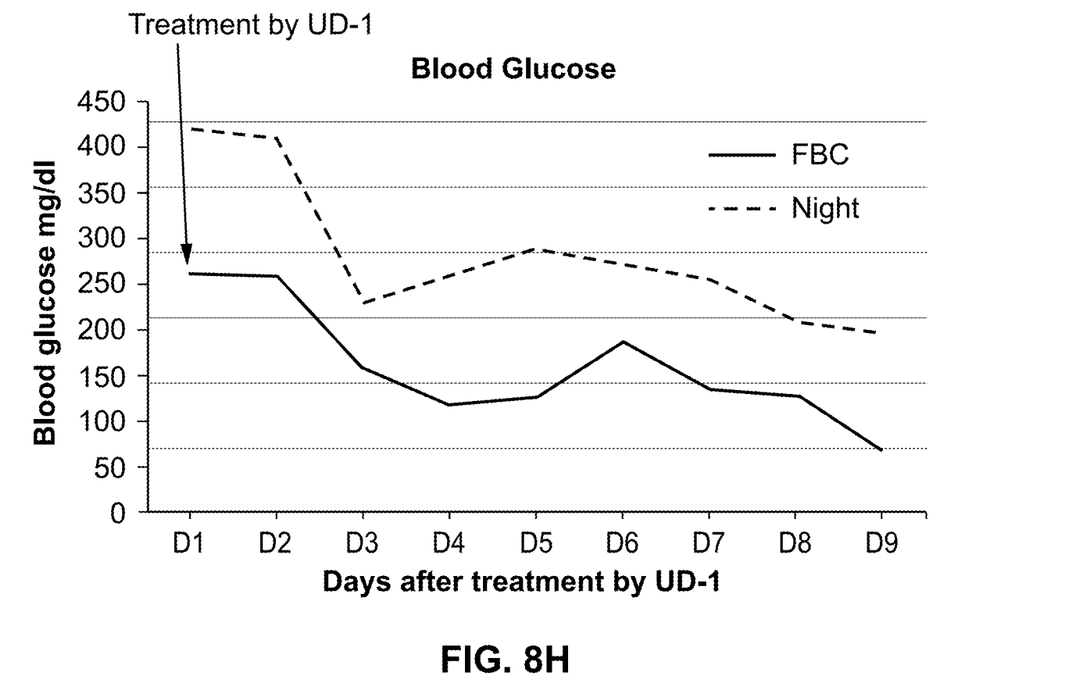
FIG. 8H shows a graph showing fasting and night blood glucose levels in a female Type 2 diabetic patient treated by Urdi-1 for five months.

FIG. 8A shows fasting and night blood glucose levels in a Type 2 diabetic male patient treated by Urdi-1 for ten days. FIG. 8B shows night blood glucose levels in a Type 2 diabetic female patient treated by Urdi-1 for two months. FIGS. 8C and 8D show fasted blood glucose levels in a Type 2 diabetic male patient treated by Urdi-1 for three months. FIGS. 8E and 8F show fasting and night blood glucose levels in a Type 2 diabetic male patient treated by Urdi-1 for three months. FIG. 8G shows fasting blood glucose levels in a female Type 2 diabetic patient treated by Urdi-1 for two months. FIG. 8H shows fasting and night blood glucose levels in a female Type 2 diabetic patient treated by Urdi-1 for five months.

Collectively, the results shown in FIG. 8 appear to demonstrate that Urdi-1 may act as an antidiabetic drug and may reverse hyperglycemia in human patients, independent of sex, and may maintain the fasted and night blood glucose levels similar to standard antidiabetic drugs (such as Glibenclamide and metformin).

EXAMPLES

Isolation and Purification of *Urtica Dioica* Extract by Thin-Layer Chromatography and HPLC Analysis In this experiment, fresh *Urtica dioica* plant was collected, and the leaves were picked up and dried at 25° C. and 75% humidity with a continuous air circulation. Then, 50 g of dried leaves was grounded and submerged in 250 mL of distilled water for 2 hours at 70° C. 10 mL of condensed vapor was fractionated using Thin-Layer Chromatography (TLC) for separation and purification of the different fractions of Urdi extract. A 200 mm·200 mm glass was coated with silica gel. Then, five spots were marked on the glass with 4 mm distance from each other, and 20 mm far from the bottom edge of the glass. Then 400 [L of the Urdi extract was loaded on each five marked spots. After drying the spots, the same process was repeated four more times in those spots. In total in each spot, 2 mL of Urdi extract was loaded. Then the glass was transferred to a chromatography tank contained water:propanol (3:1) as the solvent. The level of solvent may be about 10 mm lower than the spots. The chromatography flow may be stopped by removing the coated glass from the tank when the solvent reaches to about 30 mm below the upper edge of the coated glass. After doing TLC, three bands (representing of three fractions) appeared in the silica gel which they were cut and removed from the glass by scratching using a scalpel. Then the fractions dissolved in distilled water and centrifuged to remove the silica gel residues. All three fractions were lyophilized and stored at −80° C. These lyophilized samples were re-suspended in ddH$_2$O and used for HPLC, animal studies and metabolic assay evaluations. The resuspended sample was further purified by preparative HPLC for the structure analysis study. To end that, the fractions were injected into a reverse-phase Phenomenex Luna C-18 (10 µm, 100×8 mm) column. The mobile phase consisted of solvent A (ACN with 0.1% TFA) and solvent B (ddH$_2$O) with a flow rate of 2 mL/min. Gradient elution started with 95% solvent A, followed by a linear gradient. 20 minutes after starting, it had reached 5% of solvent A and in three minutes it reduced back to the starting composition (95% of solvent A). The injection volume was 50 µL. Fractions were detected at 225 nm.

In Vivo Experiments

Mice fasted for 16 hours before basal glucose was measured. Blood samples were taken from the heart for the pilot study, and from the tail vein for the time course study. Glucose levels in the heart and tail were determined using a glucose oxidase assay and reflectance photometry, respectively. A modified multiple (250 mg/kg body weight) STZ was used to induce beta cell death to make a diabetic mouse model. Hyperglycemia (blood glucose >200 mg/dl) was observed 2 weeks after injection in these STZ-treated mice.

Muscle Lactic Acid Assay

A muscle lactic acid assay was carried out (as previously described as the Barker and Summerson method). Lactic acid was first oxidized to acetaldehyde in hot concentrated sulfuric acid. Then the color reaction between acetaldehyde and p-hydroxydiphenyl in cold concentrated sulfuric acid was utilized for colorimetric measurement. The latter reaction was catalyzed by $Cu^{2+}$. After sacrificing the mice, their muscle tissue was separated, weighed and transferred to liquid nitrogen, followed by a TCA (10%, 10 mL/g muscle) addition. After filtration of the blended mixture, the volume reached 1 mL. The samples were transferred to a centrifuged tube and $CuSO_4$ (20%) was added and diluted by 3.5 mL distilled water. After adding 0.5 g Ca(OH)$_2$, the tubes were shaken vigorously and left at room temperature for 30 minutes before centrifugation. 6 mL of concentrated sulfuric acid and 1 mL of CuSO$_4$ (0.04%) were added to 1 mL of the supernatant of samples. The samples were incubated at 35° C. for 5 minutes and cooled to 20° C. by transferring to cold water. 0.1 mL para-phenylphenol was added, vigorously shaken and incubated at 30° C. for 30 minutes. The samples OD was read at 570 nm and the concentration of lactic acid was calculated based on a standard lactic acid sample.

N-Terminal Determination

The dansyl chloride method (DNS) for characterization of the N-terminal residue of a peptide was carried out to determine if there was a peptidic component in the Urdi-1 fraction. 5 mg of Urdi-1 were dissolved in 20 μL of 0.2 M NaHCO$_3$ and 20 μL dansyl chloride (2.5 mg/mL in acetone) and added to give 5 mM dansyl chloride, before sealing with parafilm, incubating for 1 hour at 37° C., and finally evaporation. The residue was dissolved in 50 μL of 6M HCl, sealed, and then incubated for 18 hours at 105° C. Hydrolysate and markers (dansylated standard amino acids) were spotted on different sides of a chromatography plate. These were sequentially left in the TLC tank for 30 minutes in solvent 1 [1.5% (V/V) formic acid], perpendicular to solvent 1 advancing in solvent 2 [benzene—acetic acid (9:1) (V/V)], and finally in the direction of solvent 2 advancing in solvent 3 [ethylacetate—methanol-acetic acid (20:1:1)]. Under UV light, the dansylated amino acids appeared as green spots.

Amino Acid Analysis

The amino acid content of the peptide was determined by the PICO.TAG method, which involves three steps: 1) hydrolysis of the peptide to yield a free amino acid; 2) per-column derivation of the sample; 3) analysis by reverse-phase HPLC. After the amino acid content of the sample was hydrolyzed with HCl, the released thiohydantoin amino acid derivatives from the C-terminal were analyzed by reverse-phase HPLC. In order to analyze the derived amino acids, the reverse-phase chromatogram of the sample was compared with that of standard derived amino acids (2.5 μmol/mL). With an injection volume of 10 μL, detection was carried out at 254 nm and the column temperature set to 38° C.

Formulation of Urdi-1

After discovering of the effective fraction of *Urtica dioica* extract, to administrate of that to the human subjects, Urdi-1 was formulated as a tablet (URIDIN). After considering of the all parameters such as durability and resistant to low pH and pressure, the following constituents were added to the Urdi-1 as listed in Table 1.

TABLE 1

The ingredients of the formulated tablet (URIDIN) containing Urdi-1 to administrate to the diabetic patients.

|  | % in tablet | Mass (mg) |
| --- | --- | --- |
| Urdi-1 | 7.68 | 20 |
| Avicel-102 | 29.41 | 76.58 |
| Lactose | 57.5 | 149.73 |
| Aerosil | 1.47 | 3.8 |
| Sls | 1 | 2.6 |
| Mg-st | 2.94 | 7.6 |

Clinical Study

The effect of the Urdi-1 extract was tested on six Type 2 diabetic patients. The consents were filled by patients and were reviewed by the ethical committee of Tehran Hospital. The UD1-extract (20 mg of Urdi-1) was taken orally as one or two dosages per day. Blood glucose was measured by glucometer as fasted or after dining.

Results

Separation of Aqueous Extract of *Urtica dioica* Fractions

Thin-Layer Chromatography showed the aqueous extract of Urdi to be composed of three different fractions (Urdi-1, Urdi-2 and Urdi-3) (see FIG. 2). *Urtica Dioica* fractions were detected by scanning with UV spectroscopy ranging from 190 to 300 nm. The results showed that the first fraction (Urdi-1) had a sharp peak with a strong intensity at 224 nm, while the second fraction (Urdi-2) showed a broad spectrum at 234 nm. The absorbance intensity of the third fraction (Urdi-3), detected at 284, was relatively low.

Purification and Identification of Components of Urdi-1 Fraction

Further purification of Urdi-1 was carried out by RP-HPLC fractionation (see FIG. 3). The results showed a common HPLC pattern for all purifications including one main fraction (Rt=6.10 minutes) as well as six minor fractions (Rt=3.3, 7.6, 8.1, 9.1, 13.6, 14.1 minutes). HPLC purification was carried out with waters C18 column, (5 μm, 4.6×150 mm), using a mobile phase of ACN (0.1% TFA)—deionized water, at a flow rate of 1 mL/min (injection volume: 20 μL). The fractions were detected at 224 nm. The main fraction was found to have a peptidic structure. The amino acid subfraction of the Urdi-1 was determined by the PICO.TAG method (FIG. 5)

*Urtica dioica* Extract Reduced Blood Glucose in Normal and STZ Induced Diabetic Mice

*Urtica Dioica* fractions were tested for their glucose-lowering effect in mice and the results revealed Urdi-1 to be the effective component of the three Urdi fractions (FIG. 4A). Intraperitoneal administration (25 mg/kg of body weight) of Urdi-1 extract reduced blood glucose in normal (FIG. 3B) and diabetic mice (FIG. 4C) 5 hours after injection (30%±5, n=5, p<0.05 and 50%±16, n=5, p<0.05, respectively).

Metabolic Assays

Following five hours of intraperitoneal injection of Urdi-1 (25 mg/kg body weight), normal mice (n=5) were sacrificed and their muscle and liver tissues isolated for lactic acid and glycogen determination. While lactic acid levels in muscle tissue showed significant increases (1.4 mg/g muscle±0.06 compared to control 1.06 mg/g muscle±0.07, n=8, p<0.05) neither liver glycogen nor serum insulin levels varied significantly (10.75 mg/g liver±0.23 compared to control, 9.95 mg/g liver±0.24, n=8, p<0.05) (FIG. 7A-7C).

Urdi-1 Decreased and Maintained the Level of Blood Glucose in Type 2 Diabetic Patients After getting the promising data at the animal level, we tested the efficacy of Urdi-1 in Type 2 diabetic patients. Six patients (Patient I to VI) with high level of blood glucose consented to participate in the study (Table 2). These patients were selected different sex (male and female) with varying age ranging from mid forty to late sixty. As the level of the referral blood glucose and the medication administrated by their physicians were different data of each patient is presented individually.

TABLE 2

The specification of patients treated by Urdi-1. The time diagnosed with Type 2 diabetes before treatment with Urdi-1 and the durance of treatment by Urdi-1 for each patient have been mentioned in the table.

| Patient # | Gender | Age | Time diagnosis with T2D | Time treated by Urdi-1 | Side-effect |
|---|---|---|---|---|---|
| Patient I | Male | 53 | 2 Months | 2 Weeks | N/O* |
| Patient II | Female | 65 | 4 Years | 2 Months | N/O |
| Patient III | Male | 42 | 3 Years | 3 Years | N/O |
| Patient IV | Male | 53 | 3 Months | 4 Weeks | N/O |
| Patient V | Female | 49 | 2 Months | 1 Weeks | N/O |
| Patient VI | Female | 54 | 5 Months | Ten days | N/O |

*Not Observed

Patient I was a type 2 male aged 53 and diagnosed for two months, with fasting blood glucose 285 mg/dl and night (measure the blood glucose after dinner) blood glucose 597 mg/dl (FIG. 8A). For immediate lowering of the blood glucose to a normal level, the patient was treated by insulin injection for two weeks. Then, the treatment regime was followed by Glibenclamide and metformin, as antidiabetic drugs, administration for one month. The level of blood glucose reached about 175 and 225 mg/dL for fasting and night blood glucose level, respectively, after treatment with the antidiabetic drugs. Then the patient was treated with Urdi-1 (20 mg) as twice a day. The measuring of the blood glucose showed that Urdi-1 could maintain the level of blood glucose for 10 days in a normal level as 110 and 125 mg/dL for fasting and night measurements, respectively, implying the antidiabetic effect of Urdi-1.

Patient II was a female, aged 65 years old with Type 2 Diabetes diagnosed for 4 years. She was under treatment with Glibenclamide and Metformin for four years before treatment with Urdi-1. She changed her drug regime to Udri-1 and took Urdi-1 for 2 months (20 mg) three times a day. The measuring of night blood glucose for two months showed that the administration for two months could maintain the blood glucose in normal level as 243±31 mg/dL (FIG. 8B).

Patient III was a 42 years old man diagnosed for 3 years with Type 2 diabetes and treated by Glibenclamide for 3 years. He was taking three doses (5 mg each dose) of Glibenclamide for three years and he changed the drug regime to one dose Glibenclamide (5 mg) and one dose Urdi-1 (20 mg) for three months. The blood glucose measuring for three months showed that the replacing of one dose of Glibenclamide with Urdi-1 could maintain the blood glucose in the level of normoglycemia (145.67 mg/dl). Besides, the patient did not show any side effect during Urdi-1 consumption. As shown in FIGS. 8C and 8D, the stopping of the administration of the antidiabetic drugs could increase the level of fasted blood glucose to 174.75 mg/dl. Changing of the drug regime to the Urdi-1 as two doses (20 mg per each dose) per day with no Glibenclamide could maintain the level of blood glucose as normal level similar to the level obtained with two doses of Glibenclamide (FIG. 7D).

Patient IV was a male Type 2 diabetic patient, aged 53 years old diagnosed for 3 months with fasting blood glucose 300 mg/dL and night blood glucose 449 mg/dL (FIGS. 8E and 8F). For immediate lowering of the blood glucose to the normal level, the patient was treated by insulin injection for 17 days. Then, the treatment regime was followed by Glibenclamide and metformin administration for two weeks as antidiabetic drugs. The level of blood glucose reached about 90 and 220 mg/dL for fasting and night blood glucose, respectively, after treatment with the antidiabetic drugs. Then the patient was treated with Urdi-1 (20 mg) three times a day. The measuring of the blood glucose showed that Urdi-1 could maintain the level of Fasting Blood Glucose as 125 mg/dL.

Patient V was a female Type 2 diabetic patient, aged 49 years old diagnosed for two months and treated with Glibenclamide for two months. Then the drug regime was shifted to Urdi-1 when the blood glucose level reached to 265 mg/dL (FIG. 8G). The treatment of the patient with Urdi-1 as three doses (20 mg each dose) daily could reverse the hyperglycemia to 123 mg/dL just one week after treatment.

Patient VI was a female Type 2 diabetic patient, aged 54 years old diagnosed for five months and treated with Glibenclamide and metformin for five months. Then the drug regime was changed to Urdi-1 when the blood glucose level reached to fasted level 271 mg/dL and night level 410 mg/dL (FIG. 8H). The treatment of the patient with Urdi-1 as three doses (20 mg each dose) daily could reverse the hyperglycemia to fasted level 89 mg/dL and night level 212 mg/dL in ten days after treatment.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

What is claimed is:

1. A method of isolating an extract of *Urtica dioica*, the method comprising:
    a) drying a raw material comprising *Urtica dioica*;
    b) grinding the raw material to form a ground raw material having a particle size in a range of about 0.5 to 1 mm;
    c) mixing the ground raw material with water to form a mixed raw material solution; and
    d) heating the mixed raw material solution to a temperature of about 100° C. and maintaining the temperature of about 100° C. for a period of time to form an extracted liquid solution that includes the extract of *Urtica dioica* and has a concentration of an Urdi-1 extract that is not less than 250 mg/L.

2. The method of claim 1, further comprising lyophilizing the extracted liquid solution.

3. The method of claim 1, wherein the drying occurs at a temperature in a range of about 20° C. to 30° C.

4. The method of claim 3, wherein the drying occurs at a temperature of about 25° C.

5. The method of claim 1, wherein the *Urtica dioica* is dried for a duration in a range of about 1 to 15 days.

6. The method of claim 5, wherein the *Urtica dioica* is dried for a duration of about 7 days.

7. The method of claim 1, wherein the ground raw material is mixed with water in a ratio in a range of about 1 kg of ground raw material to 3 kg of water to form the mixed raw material solution.

* * * * *